(12) United States Patent
Millward

(10) Patent No.: US 11,969,270 B2
(45) Date of Patent: Apr. 30, 2024

(54) MEDICAL INSTRUMENT STORAGE DEVICE

(71) Applicant: Lori Millward, Saint Johns, FL (US)

(72) Inventor: Lori Millward, Saint Johns, FL (US)

(*) Notice: Subject to any disclaimer, the term of this patent is extended or adjusted under 35 U.S.C. 154(b) by 0 days.

(21) Appl. No.: 17/748,130

(22) Filed: May 19, 2022

(65) Prior Publication Data
US 2023/0248460 A1 Aug. 10, 2023

Related U.S. Application Data

(60) Provisional application No. 63/308,611, filed on Feb. 10, 2022.

(51) Int. Cl.
*A61B 50/20* (2016.01)
*A61M 5/14* (2006.01)
*F16L 3/22* (2006.01)

(52) U.S. Cl.
CPC .......... *A61B 50/20* (2016.02); *A61M 5/1418* (2013.01); *F16L 3/221* (2013.01)

(58) Field of Classification Search
CPC ... A61B 50/20; A61M 5/1418; A61M 5/1414; A61M 5/1415; A61M 5/1417; F16B 13/221; A61G 7/05; F16L 3/221
USPC ...... 248/74.1, 230.6, 231.71, 229.25, 229.15
See application file for complete search history.

(56) References Cited

U.S. PATENT DOCUMENTS

| | | | | |
|---|---|---|---|---|
| 2,696,963 | A * | 12/1954 | Shepherd | A61M 5/1417 24/339 |
| 2,787,431 | A * | 4/1957 | Smith | A01K 97/10 248/231.71 |
| 2,913,740 | A * | 11/1959 | Eldridge | A61G 7/0503 24/339 |
| 3,709,556 | A * | 1/1973 | Allard | A61M 5/1415 297/188.2 |
| 4,177,967 | A * | 12/1979 | Marchus | F16M 13/04 396/420 |
| 4,387,873 | A * | 6/1983 | Pavlo | A61M 5/1415 248/231.71 |
| 4,617,919 | A * | 10/1986 | Suhre | A61G 5/128 128/845 |
| 4,640,275 | A * | 2/1987 | Buzzese | A61F 5/05883 128/845 |
| 5,336,179 | A * | 8/1994 | Ryan | F16L 3/223 604/80 |

(Continued)

*Primary Examiner* — Nkeisha Smith
(74) *Attorney, Agent, or Firm* — Brennan, Manna & Diamond, LLC

(57) ABSTRACT

The present invention relates generally to the field of medical instrument storage. More specifically, the present invention relates to a medical instrument storage device that is comprised of a frame, a main clamp attached to the frame, and at least one instrument clamp also attached to the frame. The frame of the device is generally rectangular and the device is sturdy and sterile such that the device can attach to an operating table to be used in a surgical operating room. Further, the device is comprised of at least one instrument clamp that may store medical instruments or the wires of medical instruments that are to be used during the medical procedure. In this manner, the device can be applied to any medical procedure such that necessary medical instruments may be within an easily accessible range for the surgeon or another member of the surgical team.

8 Claims, 3 Drawing Sheets

(56) References Cited

U.S. PATENT DOCUMENTS

| | | | | |
|---|---|---|---|---|
| 5,876,371 A * | 3/1999 | Yokoyama | A61M 5/1413 | 604/80 |
| 5,878,519 A * | 3/1999 | Huyck, Jr. | G09F 7/18 | 40/607.1 |
| 6,077,074 A * | 6/2000 | Homra | A61M 1/76 | 433/77 |
| 6,916,000 B2 * | 7/2005 | Weiss | A61F 9/0017 | 248/68.1 |
| 6,951,325 B2 * | 10/2005 | Lopez-Apodaca | A47B 21/0371 | 248/118.1 |
| 7,114,714 B2 * | 10/2006 | Wong | B25B 5/147 | 269/45 |
| 9,511,185 B2 * | 12/2016 | Slaker | A61M 5/1418 | |
| 10,583,243 B2 * | 3/2020 | Burke | A61M 25/02 | |
| 10,857,331 B2 * | 12/2020 | Moudy | A61M 5/1418 | |
| 11,013,395 B2 * | 5/2021 | Gupta | A61B 1/06 | |
| 2005/0006534 A1 * | 1/2005 | Shillings | F16L 3/223 | 248/68.1 |
| 2006/0230540 A1 * | 10/2006 | Whelan | A61G 7/053 | 5/662 |
| 2006/0249635 A1 * | 11/2006 | Newkirk | A61G 7/0503 | 248/74.1 |
| 2008/0243089 A1 * | 10/2008 | Keaton | F16L 55/10 | 604/250 |
| 2008/0294117 A1 * | 11/2008 | Ware | A61M 5/1418 | 604/174 |
| 2011/0210215 A1 * | 9/2011 | Nitsche | F16L 3/24 | 248/74.1 |
| 2012/0097805 A1 * | 4/2012 | Goumas | F16L 3/227 | 248/69 |
| 2014/0191103 A1 * | 7/2014 | Simon | F16M 13/022 | 248/558 |
| 2014/0259557 A1 * | 9/2014 | Egan | A61B 50/20 | 24/335 |
| 2015/0141962 A1 * | 5/2015 | Collins | A61M 25/02 | 604/513 |
| 2015/0144746 A1 * | 5/2015 | Stewart | A61M 5/1418 | 29/428 |
| 2020/0023120 A1 * | 1/2020 | Fischer | A61M 5/1415 | |

* cited by examiner

MEDICAL INSTRUMENT STORAGE DEVICE

CROSS-REFERENCE TO RELATED APPLICATION

The present application claims priority to, and the benefit of, U.S. Provisional Application No. 63/308,611, which was filed on Feb. 10, 2022, and is incorporated herein by reference in its entirety.

FIELD OF THE INVENTION

The present invention relates generally to the field of medical instrument storage. More specifically, the present invention relates to a medical instrument storage device that is comprised of a frame, a main clamp attached to the frame, and at least one instrument clamp also attached to the frame. The frame of the device is generally rectangular and the device is sturdy and sterile such that the device can attach to an operating table to be used in a surgical operating room. Further, the device is comprised of at least one instrument clamp that may store medical instruments or the wires of medical instruments that are to be used during the medical procedure. In this manner, the device can be applied to any medical procedure such that necessary medical instruments may be within an easily accessible range for the surgeon or another member of the surgical team. Accordingly, the present disclosure makes specific reference thereto. Nonetheless, it is to be appreciated that aspects of the present invention are also equally applicable to other like applications, devices and methods of manufacture.

BACKGROUND

Operating in the sterile field of a surgical operating room can cause inconveniences related to the storage and use of medical equipment. The medical equipment may not come into contact with any person or anything outside of the sterile field. If so, that object or equipment cannot be used during the procedure. Other medical equipment may be comprised of long pieces or wires that may get bent or tangled together during the procedure, thereby decreasing the efficiency of the surgeon. As a result, it is imperative to have all items that are to be used during a medical procedure cleaned and accounted for such that no harm may be done when operating on a patient. In addition, sharp medical instruments are often used during surgery. Said instruments may injure medical professionals if they are knocked off of a surgical tray during a procedure or are cluttered with other medical instruments.

Therefore, there exists a long-felt need in the art for an improved medical instrument storage device. There also exists a long-felt need in the art for a medical instrument storage device that can be easily cleaned and attached to the operating table for ease of access by the surgeon or other members of the medical team while remaining within the sterile field. Further, there exists a long-felt need in the art for a medical instrument storage device that can store a variable number of medical instruments, allowing the device to be surgery-specific. In addition, there exists a long-felt need in the art for a medical instrument storage device that can store handheld medical instruments of all shapes and sizes such that most standard medical instruments can be within reachable distance of the surgeon or another member of the medical team.

The subject matter disclosed and claimed herein, in one embodiment thereof, comprises a medical instrument storage device. The device is primarily comprised of a frame, a main clamp attached to the frame, and at least one instrument clamp also attached to the frame. The frame of the device is generally rectangular and the device is sturdy and sterile such that the device can attach to an operating table to be used in a surgical operating room. Further, the device is comprised of at least one instrument clamp that may store medical instruments or the wires of medical instruments that are to be used during the medical procedure. In this manner, the device can be used during any medical procedure such that necessary medical instruments may be within an easily accessible range for the surgeon or another member of the surgical team while remaining sterile.

In this manner, the medical instrument storage device of the present invention accomplishes all the foregoing objectives and provides an improved means to store medical instruments within the sterile field by attaching to the operating table of a surgical operating room. Further, the device can be surgery-specific such that it can only hold the medical instruments that are needed for the surgery being performed as to not clutter the operating room. In addition, the device can store handheld medical instruments of many different shapes and sizes at a distance that is easily accessible for the surgeon or another member of the medical team.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a medical instrument storage device. The device is primarily comprised of a frame, a main clamp attached to the frame, and at least one instrument clamp also attached to the frame. In differing embodiments, the frame may be of any length, width, height, or other dimension. However, in the preferred embodiment the frame is generally rectangular. The device may also be made of a plurality of materials that may be commonly used for making medical instruments. However, the device is preferably made of a medical-grade sterile metal material.

The device is comprised of a generally rectangular frame that may be attached to an arm of an operating table, or the operating table itself. At least one main clamp may be fixedly or removably attached to the frame and is further comprised of a bottom portion, a shaft, an at least one foot, and an at least one handle. The main clamp may also be generally C-shaped, such that the main clamp may fit around the arm of the operating table. To attach to the arm of the operating table, a threaded shaft may insert into a threaded continuous opening of the frame. A handle at the top of the shaft may be turned, pushing the shaft through the bottom surface of the frame and into contact with the arm. Together, the shaft and the bottom portion of the main clamp compress the arm attaching the device to the operating table. Both the shaft and the bottom portion of the main clamp may be further comprised of a foot, such that the foot is the portion of each component that contacts the arm of the operating table. The foot may be made of a material that is not damaging to the arm or it may be textured to aid in grip and traction.

The device is also comprised of an at least one instrument clamp that may be removably attached to the frame of the device. The instrument clamp may be further comprised of a body, an opening, an at least one fastener, an at least two jaws each with an at least one ridge. The body of the instrument clamp forms an opening allowing the instrument clamp to slide onto the frame and be repositioned easily along the frame. The fastener may temporarily fix the position of the instrument clamp along the frame once a desirable position is found. At least two jaws then extend out of the body of the instrument clamp and away from the frame. Each jaw is comprised of ridges that can hold medical instruments or the wires of medical instruments. The jaws may be fixed or attached via an at least one hinge, allowing them to open and close around the medical instruments. Further, the ends of the jaws may be beveled to make it easier for medical instruments to be squeezed into the ridges or for the jaws to open and close in differing embodiments.

Accordingly, the medical instrument storage device of the present invention is particularly advantageous as it allows medical instruments to be stored on the operating table of a surgical operating room. Further, the device can store medical instruments of many differing shapes and sizes at a distance that is easily accessible for the surgeon or another member of the medical team. In addition, the device is customizable in that it may only store the medical instruments that are needed for the specific surgery being performed at that time. In this manner, the medical instrument storage device overcomes the limitations of existing medical instrument storage equipment known in the art.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION

Figure 1:
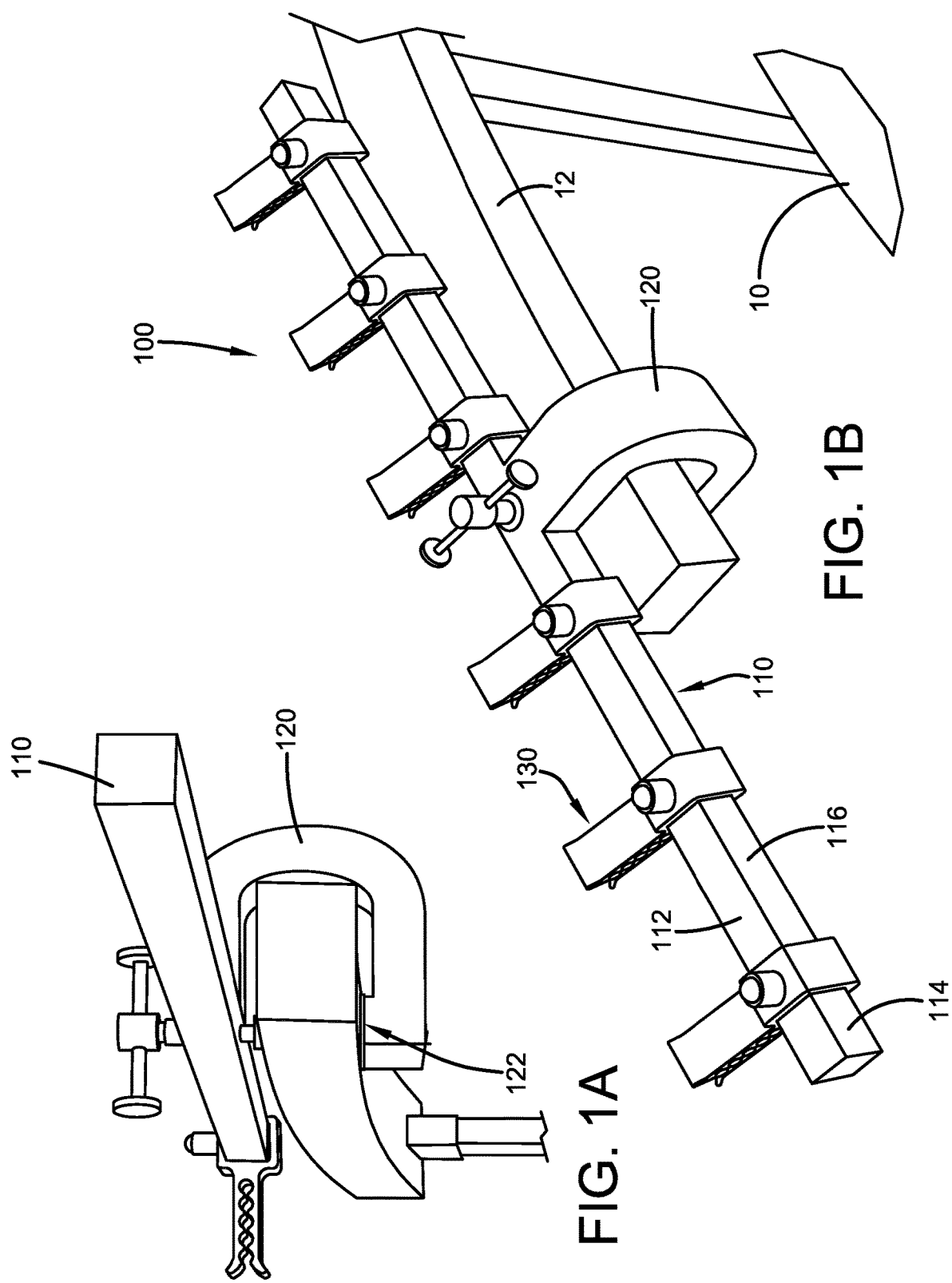
FIGS. 1A and 1B illustrate multiple perspective views of one potential embodiment of a medical instrument storage device of the present invention while attached to an arm of an operating table in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long-felt need in the art for an improved medical instrument storage device. There also exists a long-felt need in the art for a medical instrument storage device that can be easily cleaned and attached to the operating table for ease of access to the surgeon or other members of the medical team while remaining within the sterile field. Further, there exists a long-felt need in the art for a medical instrument storage device that can store a variable number of medical instruments, allowing the device to be surgery-specific. In addition, there exists a long-felt need in the art for a medical instrument storage device that can store handheld medical instruments of all shapes and sizes, such that most standard medical instruments can be within reachable distance of the surgeon or another member of the medical team.

The present invention, in one exemplary embodiment, is comprised of a medical instrument storage device that attaches to the operating table of a surgical operating room, such that the medical instruments stored in the device are easily accessible to the surgeon and within the sterile field of the procedure. The device is primarily comprised of a frame, a main clamp attached to the frame, and at least one instrument clamp also attached to the frame. In differing embodiments, the frame may be of any length, height, width, or other dimension, but in the preferred embodiment, the frame is generally rectangular. The device may also be made of a plurality of materials commonly used in medical devices but is preferably made of a medical-grade sterile metal material.

Further, the device is comprised of a generally rectangular frame with a top surface, a bottom surface, and at least two side surfaces. Together, the surfaces provide a stable and sturdy surface for other components to attach to the frame as well as allowing the frame to attach to other components or pieces of equipment. The frame may attach to an arm of an operating table via an at least one main clamp. In differing embodiments, the frame may attach directly to the operating table or another component of the operating table other than the arm. The main clamp may be fixedly or removably attached to the frame and is further comprised of a bottom portion, a shaft, an at least one foot, and an at least one handle. The main clamp may be a generally C-shaped structure. The bottom portion of the main clamp may contact the bottom surface of the arm of the operating table. A foot may be fixedly or removably attached to the bottom portion of the main clamp where it contacts the arm of the operating table. The foot may be textured or made of rubber or a similar material to aid in grip and to prevent damaging the frame. Further, a shaft may insert into a threaded continuous opening of the frame. A handle at the top of the shaft may be twisted to extend the shaft through the bottom surface of the frame to contact the arm of the operating table. By twisting the handle, the shaft and the bottom portion of the main clamp may compress the arm of the operating table attaching the device to the arm of the operating table. To detach the device from the arm of the operating table, the handle may be twisted in the opposite direction to relieve the compressive force from the shaft and the bottom portion of the main clamp. In addition, the end of the shaft that contacts the arm of the operating table may be further comprised of a foot that is made of a material to prevent damage to the arm of the operating table as well as provide additional grip.

An at least one instrument clamp may also be attached to the frame of the device. The instrument clamp may be further comprised of a body, an opening, an at least one fastener, an at least two jaws, and an at least one ridge on each jaw. The body of the instrument clamp forms an opening from which the instrument clamp may slide onto an end of the frame and be fixed at any place on the frame. The fastener may be fixedly or removably attached to the top of the body of the instrument clamp such that twisting the fastener generates a compressive force on the frame that attaches the instrument clamp to the frame of the device. The body of the instrument clamp then extends outwards from the frame in the form of two jaws. Each jaw may be comprised of an at least one ridges which can be used to store various medical instruments as well as the wires of those medical instruments. In one potential embodiment, the jaws may be fixed, such that wires or other medical instruments may be set or squeezed into the ridges to be stored. In another potential embodiment, the jaws may be attached to the body via an at least one hinge, allowing them to open and close to fit medical instruments of varying sizes and shapes more easily. In addition, the ends of the jaws may be beveled to allow the instruments to easily slide into the ridges of the jaws or to allow the person to easily open the jaws, in differing embodiments.

Accordingly, the medical instrument storage device of the present invention is particularly advantageous as it allows medical instruments to be stored on the operating table of a surgical operating room. Further, the device can be customized to be used in different surgeries by only storing those medical instruments that are needed during the surgery being performed at that time. In addition, the device can store medical instruments of many shapes and sizes as well as the wires of the medical instruments within an easily accessible range of the surgeon or other member of the medical team. Therefore, the device may not break the sterile field of the operating room.

Referring initially to the drawings, FIG. 1 illustrates multiple perspective views of one potential embodiment of a medical instrument storage device 100 of the present invention while attached to an arm 12 of an operating table 10 in accordance with the disclosed architecture. The device 100 is primarily comprised of a frame 110, a main clamp 120 attached to the frame, and at least one instrument clamp 130 also attached to the frame 110. In differing embodiments, the frame 110 may be of any length, width, height, or other relevant dimension and may be of any general shape such as, but not limited to: a rectangle, a square, a triangle, a circle, an oval, a cylinder, a prism, a pentagon, a trapezoid, a diamond, etc. Further, the device 100 may be made of a plurality of materials such as plastic or metal, but is preferably made of a medical-grade sterile metal material such as, but not limited to: stainless steel, titanium, cobalt chrome, aluminum, magnesium, etc. However, the device 100 may be made of any material that can endure high level disinfection such as but not limited to steam pressure cleaning.

In the preferred embodiment of the device 100, the frame 110 is generally rectangular and comprised of a top surface 112, a bottom surface 114, at least two side surfaces 116, and an at least one threaded continuous opening 118. At least one generally C-shaped main clamp 120 may be fixedly or removably attached to the frame 110, allowing the device 100 to attach to an arm 12 of an operating table 10, endoscopy cart, stretcher, etc. In differing embodiments, the main clamp 120 may attach to any part of the operating table 10 that keeps the device 100 within reach of the surgeon or another member of the medical team. The main clamp 120 is further comprised of a bottom portion 122, a shaft 124, an at least one foot 126, and an at least one handle 128. The main clamp 120 may be placed around the arm 12 of an operating table 10. The shaft 124, which may be threaded, may insert into a threaded or non-threaded continuous opening 118 of the top surface 112 of the frame 110. A handle 128 may be fixedly attached to the shaft 124 such that when the handle 128 is turned in one direction (ex., clockwise), the mating threads of the shaft 124 and the threads of the continuous opening 118 of the frame 110 may push the shaft 124 downwards through the bottom surface 114 of the frame 110. The handle 128 may be generally T-shaped in the preferred embodiment but may be of any shape in differing embodiments that aids in turning the shaft 124. The shaft 124 may then generate a compressive force on the arm 12 of the operating table 10 with the bottom portion 122 of the main clamp 120. Both the shaft 124 and the bottom portion 122 may be comprised of a foot 126 which covers the portion of the shaft 124 and the bottom portion 122 that contacts the arm 12. The foot 126 may be made of a soft material, such as rubber, felt, etc., that may not damage the arm 12. In addition, the foot 126 may be textured or made of a material that aids in grip and traction to better retain the device 100 to the arm 12 of the operating table 10. The foot 126 may also be removable for cleaning purposes.

Figure 2:
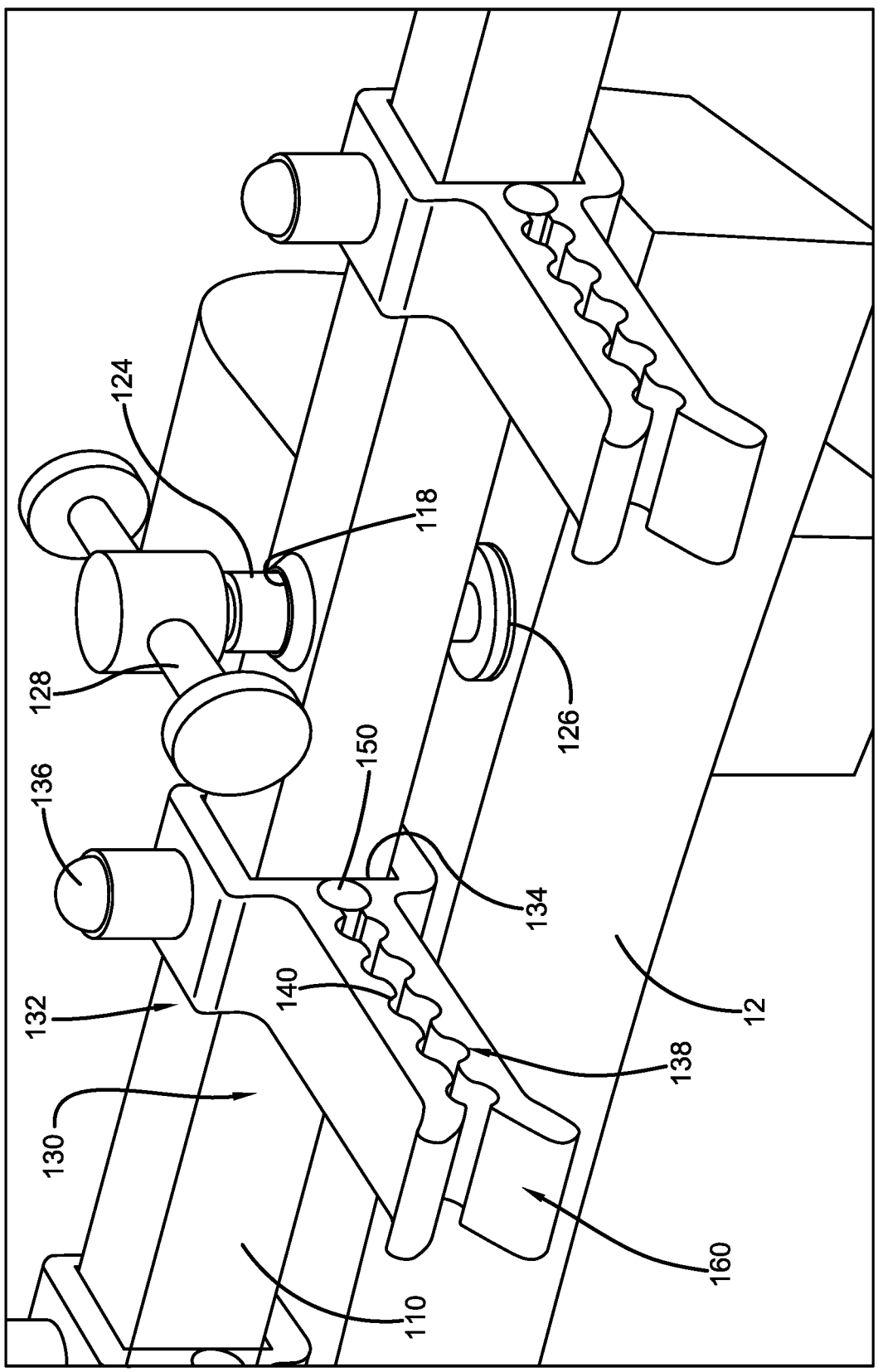
FIG. 2 illustrates an enhanced perspective view of the instrument jaws of one potential embodiment of a medical instrument storage device of the present invention while attached to an arm of an operating table in accordance with the disclosed architecture.

FIG. 2 illustrates an enhanced perspective view of the instrument jaws 138 of one potential embodiment of a medical instrument storage device 100 of the present invention while attached to an arm 12 of an operating table 10 in accordance with the disclosed architecture. An at least one instrument clamp 130 may be removably attached to the frame 110 of the device 100. The instrument clamp 130 may be further comprised of a body 132, an opening 134, an at least one fastener 136, and at least two jaws 138 each with at least one ridge 140. The body 132 of the instrument clamp 130 may form an opening 134 from which the instrument clamp 130 may slide onto the frame 110 from one of the ends of the frame 110. Once the instrument clamp 130 has been slid into a desirable position along the frame 110, a fastener 136 may be tightened to fasten the instrument clamp 130 to a fixed position. The fastener 136 may be any fastener known in the art such as, but not limited to: a hinge, a screw, a bolt, a magnet, a hook-and-loop fastener, etc. In the preferred embodiment, the fastener 136 is on the top surface of the body 132 and, when twisted (ex., clockwise), generates a compressive force on the top surface 112 and bottom surface 114 of the frame 110.

Figure 3:
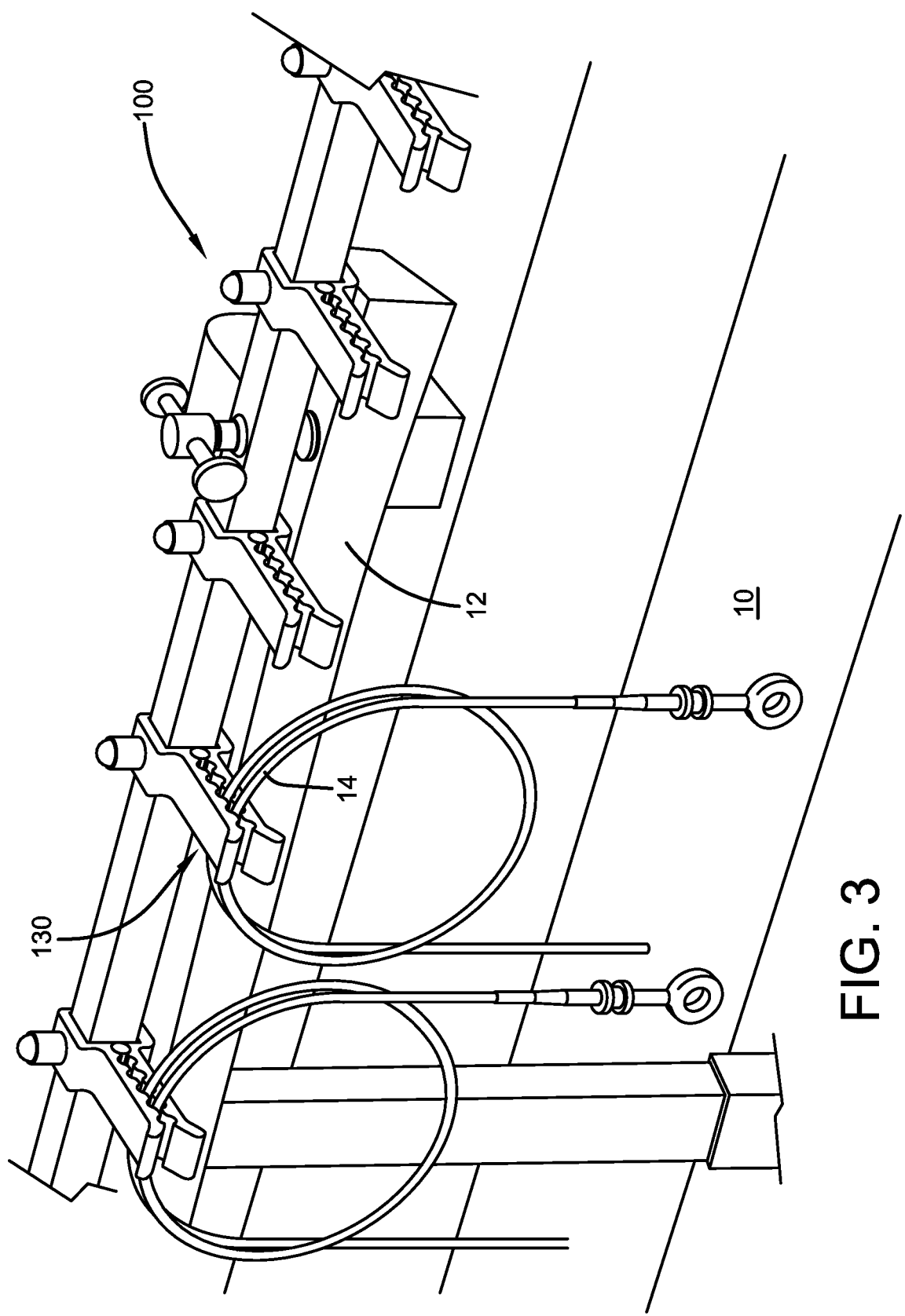
FIG. 3 illustrates a perspective view of one potential embodiment of a medical instrument storage device of the present invention while attached to an arm of an operating table and while holding a medical instrument in accordance with the disclosed architecture.

FIG. 3 illustrates a perspective view of one potential embodiment of a medical instrument storage device 100 of the present invention while attached to an arm 12 of an operating table 10 and while holding a medical instrument 14 in accordance with the disclosed architecture. The body 132 of the instrument clamp 130 then extends outwards from the frame 110 in the form of two jaws 138. Each jaw 138 may be comprised with an at least one ridge 140, but preferably multiple ridges 140, that can grab and contact medical instruments 14 or the wires of medical instruments 14. In one potential embodiment, the jaws 138 may be fixedly attached to the body 132, in which medical instruments may be pressed or squeezed into the ridges 140 of the jaws 138 to be stored. In another potential embodiment, the jaws 138 may be attached to the body 132 of the instrument clamp 130 via an at least one hinge 150, allowing one or both the jaws 138 to open and close around medical instruments 14. In this embodiment, the jaws 138 may be able to easily accept medical instruments 14 of various size, shape, and orientation. Further, the ends 160 of the jaws 138 are preferably beveled to allow for medical instruments 14 to more easily be inserted into the ridges 140 of the jaws 138. The beveled edges of the jaws 138 may also allow a user to easily open the jaws 138 in the embodiment in which the jaws 138 are attached to the body 132 of the instrument clamp 130 via a hinge. In this manner, potentially sharp instruments 14 are stored in an organized manner such that a medical professional cannot be accidently pierced by said instruments 14.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "medical instrument storage device" and "device" are interchangeable and refer to the medical instrument storage device 100 of the present invention.

Notwithstanding the foregoing, the medical instrument storage device 100 of the present invention and its various components can be of any suitable size and configuration as is known in the art without affecting the overall concept of the invention, provided that they accomplish the above-stated objectives. One of ordinary skill in the art will appreciate that the size, configuration and material of the medical instrument storage device 100 as shown in the FIGS. are for illustrative purposes only, and that many other sizes and shapes of the medical instrument storage device 100 are well within the scope of the present disclosure. Although the dimensions of the medical instrument storage device 100 are important design parameters for user convenience, the medical instrument storage device 100 may be of any size, shape and/or configuration that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A medical instrument storage device comprising:
    a frame having a continuous opening;
    a C-shaped main clamp attached to the frame;
    a shaft further comprised of a handle and a foot, wherein the shaft extends through the continuous opening of the frame; and
    an instrument clamp that is repositionable along the frame and that is further comprised of a fastener and a pair of jaws, wherein the pair of jaws attach to the instrument clamp via a hinge.

2. The medical instrument storage device of claim 1, wherein each of the pair of jaws is comprised of a ridge.

3. The medical instrument storage device of claim 1, wherein the instrument clamp is comprised of an opening that allows the instrument clamp to fit over the frame.

4. The medical instrument storage device of claim 1, wherein the fastener of the instrument clamp allows the instrument clamp to be tightened along the frame.

5. The medical instrument storage device of claim 4, wherein the fastener is a screw.

6. The medical instrument storage device of claim 1, wherein the foot of the shaft is comprised of a rubber material.

7. The medical instrument storage device of claim 1, wherein the medical instrument storage device is comprised of a medical-grade metal material.

8. The medical instrument storage device of claim 1, wherein the handle of the shaft is generally T-shaped.

* * * * *